US006333432B1

(12) United States Patent
Fitzpatrick et al.

(10) Patent No.: US 6,333,432 B1
(45) Date of Patent: Dec. 25, 2001

(54) FUNGICIDAL COMPOSITIONS AND METHODS, AND COMPOUNDS AND METHODS FOR THE PREPARATION THEREOF

(76) Inventors: Gina M. Fitzpatrick, 304 W. Columbine La., Westfield, IN (US) 46074; Ann B. Orth, 77 Wood Stream Dr., Langhorne, PA (US) 19053-1507; Maurice C. H. Yap, 22 Chestnut Ct.; Richard B. Rogers, 1957 Camargue Dr., both of Zionsville, IN (US) 46077; Todd L. Werk, 8820 Yardley Ct. #312, Indianapolis, IN (US) 46268; George E. Davis, 15114 Count Fleet Ct., Carmel, IN (US) 46032

( * ) Notice: Subject to any disclaimer, the term of this patent is extended or adjusted under 35 U.S.C. 154(b) by 0 days.

(21) Appl. No.: 09/562,120

(22) Filed: May 1, 2000

Related U.S. Application Data
(60) Provisional application No. 60/132,365, filed on May 4, 1999.

(51) Int. Cl.$^7$ ................ C07C 233/05; A01N 37/18
(52) U.S. Cl. ................ 564/158; 514/535; 514/496; 514/616; 560/43; 564/48
(58) Field of Search .............. 564/158, 48; 514/616, 514/596, 535; 560/43

(56) References Cited

U.S. PATENT DOCUMENTS

| | | | |
|---|---|---|---|
| 3,459,534 | 8/1969 | Dorfman | 71/118 |
| 3,994,975 | 11/1976 | Alink et al. | 260/563 |
| 5,034,393 | 7/1991 | Hackler et al. | 514/258 |
| 5,280,044 | * 1/1994 | Crowley et al. | 514/616 |
| 5,292,743 | 3/1994 | Liebeschuetz | 514/275 |
| 5,447,960 | 9/1995 | Sinnott et al. | 514/732 |

FOREIGN PATENT DOCUMENTS

| | | |
|---|---|---|
| 4110483A1 | 10/1992 | (DE) . |
| 1-228949 | 9/1989 | (JP) . |
| 3-95141 | 4/1991 | (JP) . |
| WO 97/08135 | 3/1997 | (WO) . |

OTHER PUBLICATIONS

Hutchins et al., "Stereoselective Reductions of Substituted Cyclohexyl and Cyclopentyl Carbon–Nitrogen π Systems with Hydride Reagents", *J. Org. Chem*, 1983, 48, 3412–3422.

Selwood et al., Structure–Activity Relationships of Antifilarial Antimycin Analogues: A Multivariate Pattern Recognition Study, *J. Med. Chem.*, 1990, 33, 136–142.

Neft et al., Inhibition of Electron Transport by Substituted Salicyl–N–(n–octadecyl)amides, Department of Chemistry, Utah State University, Chem. Abstr. 76, 94491e, *J. Med. Chem.* 14, 1169 (1971).

Dickie et al., The Chemistry of Antimycin A. XI. N–Substituted 3–Formamidosalicylic Amides, *J. Med. Chem.*, vol. 6, Jul. 1963, pp. 424–427.

Tokutake et al., Strucutral Factors of Antmycin A Molecule Required for Inhibitory Action, *Biochimica et Biophysica Acta*, 1185 (1994) 271–278.

Aburaki et al., Synthesis of Deisovalerylblastmycin, *Chemistry Letters*, pp. 701–704 (1976), published by Chemical Society of Japan.

Kinoshita et al., Syntheses of (3S, 4R, 15S)–4,15–Dimethyl–1,5–dioxa–3–(3'–formamidolsalicyl–amido)–cyclopentadecane–2,6–dione and its (15R)–Epimer, New Antimycin Analogs, *Bulletin of the Chemical Society of Japan*, vol. 44, No. 12, (1971).

Taborsky et al., Substituted Salicylanilides III, *J. Pharm. Sci.*, vol. 52, No. 6, (1963) pp. 542–545.

Abidi et al., Liquid chromatography–thermospray mass spectrometric study of N–acylamino dilactones and 4–butyrolactones derived from antimycin A, *J. of Chromatography*, 522 (1990) 179–194.

Miyoshi et al., A model of antimycin A binding based on structure–activity studies of synthetic antimycin A analogues, *Biochim. et Biophysica Acta* 1229 (1995) 149–154.

Xu et al., Comparison between the properties of 3–nitrosalicyl–N–alkylamide and antimycin A acting on $QH_2$: cytochrome c reductase, *Biochim. et Biophysica Acta*, 1142 (1993) 83–87.

Communication to the Editor, Journal of Antibiotics vol. 46, No. 4, (1992), pp. 701–703.

Caglioti et al., The Structure of Neoantimycin, *Tetrahedron*, vol. 25, pp. 2193–2221 (1969).

Immamura et al., Novel Antimycin Antibiotics, Urauchimycins A and B, Produced by Marine Actinomycete, J. of Antibiotics, vol. 46, No. 2 (1992).

Tokutake et al., Inhibition of electron transport of rat–liver mitochondria by synthesized antimycin A analogs, Biochemica et Biophysica Acta, 1142 (1993) 262–268.

Keizo et al., Antimcyin derivatives, *Chem. Abstracts* vol. 70, 1969, p. 310.

Makoto et al., Fungicides manufacture with streptoverticillium, *CA Selects: Fungicides*, Issue 26 (1995), p. 9.

Harada et al., Antimycin A, an antibiotic substance useful for prevention and treatment of imochibyo, a disease of rice, *15A Pesticides*, 19286, p. 1959.

Unknown number, Thionosalicylic Acid Anilides, Salts Thereof, Intermediates Therefor and Productions Processes, F. Bayer Akt., Kurz et al., South African patent application, dated Apr. 19, 1967.

* cited by examiner

*Primary Examiner*—Shailendra Kumar
(74) *Attorney, Agent, or Firm*—Carl D. Corvin; Kenneth L. Loertscher

(57) ABSTRACT

Fungicidal compositions and methods comprising acylated aminosalicylamides (AASA) described herein. Novel amines and 3-nitrosalicylamides, and their use as pesticides and in the preparation of the antifungal AASA compounds are also disclosed.

39 Claims, No Drawings

FUNGICIDAL COMPOSITIONS AND METHODS, AND COMPOUNDS AND METHODS FOR THE PREPARATION THEREOF

PRIORITY CLAIM

This application claims a priority based on provisional application 60/132,365 which was filed in the U.S. Patent and Trademark Office on May 4, 1999.

BACKGROUND OF THE INVENTION

1. Field of the Invention

The present invention relates to the field of fungicidal compounds, compositions and methods, and more particularly to plant fungicides and methods involving the application of fungicidally effective amounts of such compounds and compositions to the locus of a plant pathogen. The present invention also provides novel compounds and methods useful in the preparation of fungicides and fungicidal compositions.

2. Description of the Prior Art

Varieties of antifungal compositions and methods are well known in the art. Antimycin, for example, has been identified as a naturally occurring substance produced by Streptomnyces spp which has efficacy as a fungicide. However, there has remained a need for new fungicides. The present invention provides fungicides which have a high residual activity, greater activity at lower application rates, and a broader spectrum of efficacy.

SUMMARY OF THE INVENTION

Briefly describing one aspect of the present invention, there are provided fungicidal compounds comprising acylated aminosalicylamides of the Formula I:

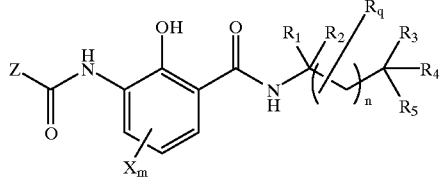

Formula I wherein m, n, q, X, Z, $R_q$ and $R_1$–$R_5$ are as hereafter defined. The invention also encompasses hydrates, salts and complexes thereof.

The present invention also provides fungicidal compositions comprising the acylated aminosalicylamides in combination with phytologically acceptable carriers and/or diluents. Methods for the use of the acylated aminosalicylamides compounds and compositions are also disclosed.

In another aspect, the present invention includes compounds and methods for preparation of the acylated aminosalicylamides. Encompassed are certain novel intermediates, including ones having fungicidal efficacy, as well as methods for the preparation thereof.

It is an object of the present invention to provide acylated aminosalicylamides and compositions thereof which are effective as antifungal agents.

Another object of the present invention is to provide methods for the control and/or prevention of fungus infestations, which methods include the application of acylated aminosalicylamides and compositions containing same.

The present invention also has as an object the provision of certain intermediates, their methods of preparation and use in producing acylated aminosalicylamides, and optionally the use of such intermediates as fungicides.

Further objects and advantages of the present invention will be apparent from the description which follows.

DESCRIPTION OF THE PREFERRED EMBODIMENT

For the purposes of promoting an understanding of the principles of the invention, reference will now be made to the embodiments illustrated herein and specific language will be used to describe the same. It will nevertheless be understood that alterations, modifications and further applications of the invention are contemplated as would normally occur to one skilled in the art to which the invention relates. The present invention particularly contemplates such compounds, compositions and methods which are substantially equivalent to the inventions claimed herein.

General Scope of the Invention

The present invention relates to various acylated aminosalicylamide ("AASA") compounds which are active as antifungal agents. Also included are formulations including the acylated aminosalicylamide compounds, and methods of using the AASA compounds and formulations. The methods of preparing the AASA compounds are also encompassed by the present invention, as well as certain intermediate compounds, and their method of preparation and optional use as fungicides.

Acylated Aminosalicylamide Compounds

The novel antifungal AASA compounds of the present invention are described by the following Formula I:

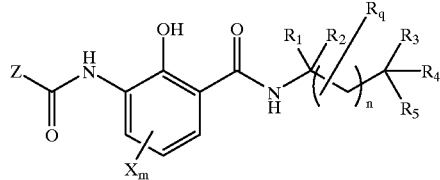

Formula I wherein:

a. m is 1 or 2;
b. ( )n represents a carbon chain including carbon atoms where n is 1 to 11;
c. q is from 0 to 2n;
d. X is hydrogen ("H"), halogen, $C_1$–$C_4$ alkyl, $C_2$–$C_4$ alkenyl, cyclopropyl, cyano, $NO_2$, $C_1$–$C_4$ haloalkyl, hydroxy, $C_1$–$C_3$ alkoxy, $C_1$–$C_3$ haloalkoxy, $C_1$–$C_3$ alkylthio, $C_1$–$C_3$ alkylsulfonyl, $C_1$–$C_3$ alkylsulfinyl, $C_1$–$C_2$ SCOalkyl, $C_1$–$C_3$ NHalkyl, $C_1$–$C_3$ N(alkyl)$_2$, $C_1$–$C_3$ NHCOalkyl, NHC(O)H, $C_1$–$C_3$ N-alkyl COalkyl, $C_1$–$C_3$ NHCONHalkyl, $C_1$–$C_2$ NHCON (alkyl)$_2$, NHC(O)$R_x$, C(O)$R_x$, C(O)O$R_x$, or C(O)N$R_x$$R_x$, in which $R_x$ is independently H or $C_1$–$C_4$ alkyl;
e. Z is H, $C_1$–$C_2$ alkyl, $CH_3$NH or $Me_2$N;
f. $R_1$ and $R_2$ may be the same or different, but at least one of $R_1$ and $R_2$ must be H or methyl, and each of $R_1$ and $R_2$ is independently selected from the group consisting of H, cyano, $C_1$–$C_4$ alkyl (straight chain or branched), $C_2$–$C_4$ alkenyl (straight chain or branched), aryl, $C_1$–$C_4$ haloalkyl (straight chain or branched), $C_1$–$C_4$ carboalkoxy, and $C_3$–$C_6$ cycloalkyl optionally substituted with one or more of $OR_6$, $SR_6$, $NR_6R_7$, halogen or cyano;

g. $R_3$, $R_4$, and $R_5$ may be the same or different and each of $R_3$–$R_5$ is independently selected from the group consisting of H, halogen, $C_1$–$C_3$ alkoxy, $C_1$–$C_3$ haloalkoxy, $C_3$–$C_6$ cycloalkoxy, aryloxy, $C(=O)R_6$ and $C(=O)OR_6$;

h. each $R_q$ can be the same or different and each $R_q$ is defined as follows:

i. any or all of $R_q$ are H, halogen, cyano, $C_1$–$C_4$ alkyl (straight chain or branched), $C_2$–$C_4$ alkenyl (straight chain or branched), aryl, $C_1$–$C_4$ haloalkyl (straight chain or branched), $C_1$–$C_4$ alkoxy (straight chain or branched), $C_1$–$C_4$ haloalkoxy (straight chain or branched), or $C_1$–$C_4$ carboalkoxy, and $C_3$–$C_6$ cycloalkyl optionally substituted with one or more of $OR_6$, $SR_6$, $NR_6R_7$, halogen or cyano;

ii. any of $R_q$ can be hydroxy provided that no two geminal $R_q$ are both hydroxy;

iii. any adjacent $R_q$ can be combined as unsaturations in the main chain to form alkenyl or alkynyl bonds as allowed by chemical bonding rules; and iv. any of geminal $R_q$ can be combined in a double bond to an oxygen;

i. the number of substituents included as $R_q$ will vary depending on n and q in accordance with chemical bonding rules;

j. $R_6$ and $R_7$ may be the same or different and each of $R_6$ and $R_7$ is selected from the group consisting of H, $C_1$–$C_4$ alkyl, $C_3$–$C_4$ alkenyl, $C_3$–$C_4$ alkynyl, $C_3$–$C_6$ cycloalkyl, aryl and $C_1$–$C_4$ alkoxyalkyl, except that $R_7$ can not be H;

k. aryl, as used herein, may be unsubstituted or may have up to three substituents selected from the group consisting of halogen, $C_1$–$C_4$ alkyl, $C_2$–$C_4$ alkenyl, $C_3$–$C_6$ cycloalkyl, cyano, $C_1$–$C_4$ haloalkyl, hydroxy, $C_1$–$C_3$ alkoxy, $C_1$–$C_3$ haloalkoxy and aryloxy; and l. when stereocenters are formed by various substitution patterns as described herein, all isomers are included in the definitions for the structure of Formula I.

The terms alkyl, alkylene, alkenylene and the like, as used herein, include within their scope both straight and branched groups, and the terms alkenyl, alkenylene and the like are intended to include groups containing one or more double bonds. The foregoing terms further contemplate either substituted or unsubstituted forms. A substituted form refers to substitution with one or more groups selected from halo, haloalkoxy, phenyl, alkoxy, carboalkoxy or amido, substituted with one or two alkyl groups.

The terms halogen and halo as used herein include chlorine, bromine, fluorine and iodine. The terms haloalkyl and the like refer to groups substituted with one or more halo atoms. It will be appreciated that certain combinations of substituent groups for compounds which fall within the definitions given herein will be impossible to prepare for steric and/or other chemical reasons. Such compounds are not included within the scope of the invention.

Various hydrates, salts and complexes of compounds of Formula I can be made in the conventional ways. For example, salts may be formed by replacing the hydroxyl hydrogen atom with a cation, for example, $NH_4^+$, $^+N(CH_3)_4$, $^+N(Bu)_4$, $K^+$, $Na^+$, $Ca^{++}$, $Li^+$, $Mg^{2+}$, $Fe^{2+}$, $Cu^{2+}$, etc. These derivatives are also useful in accordance with the present invention.

The designation ( )n in Formula I is used to indicate a carbon chain which can include "n" carbon atoms.

As is apparent from the descriptions herein, the AASA compounds are useful in a variety of forms, i.e., with various substitutions as identified. Examples of particularly desirable compounds are quite diverse, and many are mentioned herein. Included are compounds in which Z is hydrogen, and also those in which X is hydrogen or 5-fluoro. Also preferred are compounds in which at least one of $R_1$ and $R_2$ is other than hydrogen, and in which there are 1–4 $R_q$'s which are other than hydrogen and $R_{3-5}$ are all hydrogen. The number "n" of carbons in the chain is preferably from 4 to 6.

AASA Compositions

The AASA compounds are preferably applied in the form of a composition comprising one or more of the AASA compounds with a phytologically acceptable carrier. The compositions are either concentrated formulations which are dispersed in water or another liquid for application, or are dust or granular formulations which are applied without further treatment. The compositions are prepared according to procedures which are conventional in the agricultural chemical art, but which are novel and important because of the presence therein of the compounds of this invention. Some description of the formulation of the compositions is given to assure that agricultural chemists can readily prepare desired compositions.

The dispersions in which the compounds are applied are most often aqueous suspensions or emulsions prepared from concentrated formulations of the compounds. Such water-soluble, water suspendable, or emulsifiable formulations are either solids, usually known as wettable powders, or liquids, usually known as emulsifiable concentrates or aqueous suspensions. The present invention contemplates all vehicles by which the acylated aminosalicylamides can be formulated for delivery for use as a fungicide. As will be readily appreciated, any material to which the AASA compounds can be added may be used, provided they yield the desired utility without significant interference with activity of the acylated aminosalicylamides as antifungal agents.

Wettable powders, which may be compacted to form water dispersible granules, comprise an intimate mixture of the active compound, an inert carrier and surfactants. The concentration of the active compound is usually from about 10% to about 90% w/w, more preferably about 25% to about 75% w/w. In the preparation of wettable powder compositions, the toxicant products can be compounded with any of the finely divided solids, such as prophyllite, talc, chalk, gypsum, fuller's earth, bentonite, attapulgite, starch, casein, gluten, montmorillonite clays, diatomaceous earths, purified silicates or the like. In such operations, the finely divided carrier is ground or mixed with the toxicant in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds comprise a convenient concentration of the AASA compound, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of the AASA compounds, dispersed in an aqueous vehicle at a concentration in the range from about 5% to about 50% w/w. Suspensions are prepared by finely grinding the compound, and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions, which are particularly useful for applications to the soil. Granular compositions usually contain from about 0.5% to about 10% w/w of the compound, dispersed in an inert carrier which consists entirely or in large part of coarsely divided attapulgite, bentonite, diatomite, clay or a similar inexpensive substance. Such compositions are usually prepared by dissolving the compound in a suitable solvent and applying it to a granular carrier which has been pre-formed to the appropriate particle size, in the range of from about 0.5 to about 3 mm. Such compositions may also be formulated by making a dough or paste of the carrier and compound, and crushing and drying to obtain the desired granular particle.

Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% w/w of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

AASA Compositions with Other Compounds

The composition may optionally include fungicidal combinations which comprise at least 1% of one or more of the AASA compounds with another compound. Such additional compounds may be fungicides, herbicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds in combination can generally be present in a ratio of from 1:100 to 100:1.

Utility of AASA Compounds and Compositions as Fungicides

The present invention includes within its scope methods for the control or prevention of fungal attack. These methods comprise applying to the locus of the fungus, or to a locus in which the infestation is to be prevented (for example applying to grape plants), a fungicidal amount of one or more of the AASA compounds or compositions. The AASA compounds are suitable for treatment of various plants at fungicidal levels, while exhibiting low phytotoxicity. The compounds are useful in a protectant or eradicant fashion.

The AASA compounds are applied by any of a variety of known techniques, either as the compounds or as compositions including the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The AASA compounds have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi which infect useful plant crops. Activity has been demonstrated for a variety of fungi, including for example the following representative fungal species: Downy Mildew of Grape (*Plasmopara viticola*—PLASVI), Late Blight of Tomato (*Phytophthora infestans*—PHYTIN), Powdery Mildew of Wheat (*Erysiphe graminis*—ERYSGT), Brown Rust of Wheat (*Puccinia recondita*—PUCCRT), Leaf Blotch of Wheat (*Septoria tritici*—SEPTTR), Glume Blotch of Wheat (*Septoria nodorum*—LEPTNO), Rice Blast (*Pyricularia oryzae*—PYRIOR), Apple Scab (*Venturia*

*inaequalis*—VENTIN), and cultures of *Gloeophyllum trabeum* (LENZTR), *Trametes versicolor* (CORLVE), *Postia placenta* (POSTPL), *Trametes lilacino-gilva* (TRAMLI), and *Chaetomium globosum* (CHATGL). It will be understood by those in the art that the efficacy of the AASA compounds for the foregoing fungi establishes the general utility of the compounds as fungicides.

The AASA compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the AASA compounds, and compositions containing the same, may not be equally effective at similar concentrations or against the same fungal species.

The AASA compounds and compositions are effective in use with plants in a disease inhibiting and phytologically acceptable amount. The term "disease inhibiting and phytologically acceptable amount" refers to an amount of a compound which kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre.

Preparation of Compounds
AASA Intermediates

The AASA compounds are preferably produced from corresponding amines and 3-nitrosalicylamides. In a preferred process, the acylated aminosalicylamides are obtained by reaction of a 3-aminosalicylamide with acetic-formic anhydride. The 3-aminosalicylamide is prepared by hydrogenation of a 3-nitrosalicylamide derived from reaction of a 2-hydroxy-3-nitrobenzoyl chloride with the appropriate amine. It is therefore an aspect of the present invention to provide the amines and 3-nitrosalicylamides which are useful in preparation of the AASA compounds. In addition, the 3-nitrosalicylamides have fungicidal activity. A description of the general preparation of the amines from the corresponding aldehyde, acid or alcohol, and the consequent production of the related 3-nitrosalicylamides, is provided hereafter.

General Preparation of Acylated Aminosalicylamides

A preferred synthesis of the desired product acylated aminosalicylamides (Formula I) is shown in the following Scheme 1. 2-Hydroxy-3-nitrobenzoic acid 1 was converted to the acid chloride 2 with excess thionyl chloride. After removal of the excess thionyl chloride, the crude acid chloride 2 was reacted with the desired amine 3 in dichloromethane solution containing triethylamine as an acid scavenger and 4-dimethylaminopyridine (DMAP) as a catalyst. Crude 3-nitrosalicylamide 4 could be isolated after washing the reaction mixture with dilute HCl solution, drying, and evaporation of the solvent. Usually 4 was of sufficient purity to carry forward to the final product 6, but if desired could be purified by recrystallization or chromatography or a combination of both. In some cases where the 3-nitrosalicylamide 4 is a mixture of diastereomers, one might choose to isolate the individual diastereomers at this stage. However, since all of the various diastereomers are fungicidally active, this is not necessary. The 3-nitrosalicylamide 4 was subsequently reduced under catalytic hydrogenation conditions using Pd, Pt, or Ni catalysts either unpoisoned or poisoned with sulfur or lead. The 3-aminosalicylamide 5 usually was not isolated, but immediately reacted with excess acetic-formic anhydride. Isolation of the AASA product 6 was a simple matter of filtration, washing with sodium bicarbonate solution, drying and evaporation of the solvent. The crude product 6, usually a solid foam or glass, often was of sufficient purity to be directly submitted for testing. However, if desired, it could be further purified by recrystallization or chromatography or a combination of both.

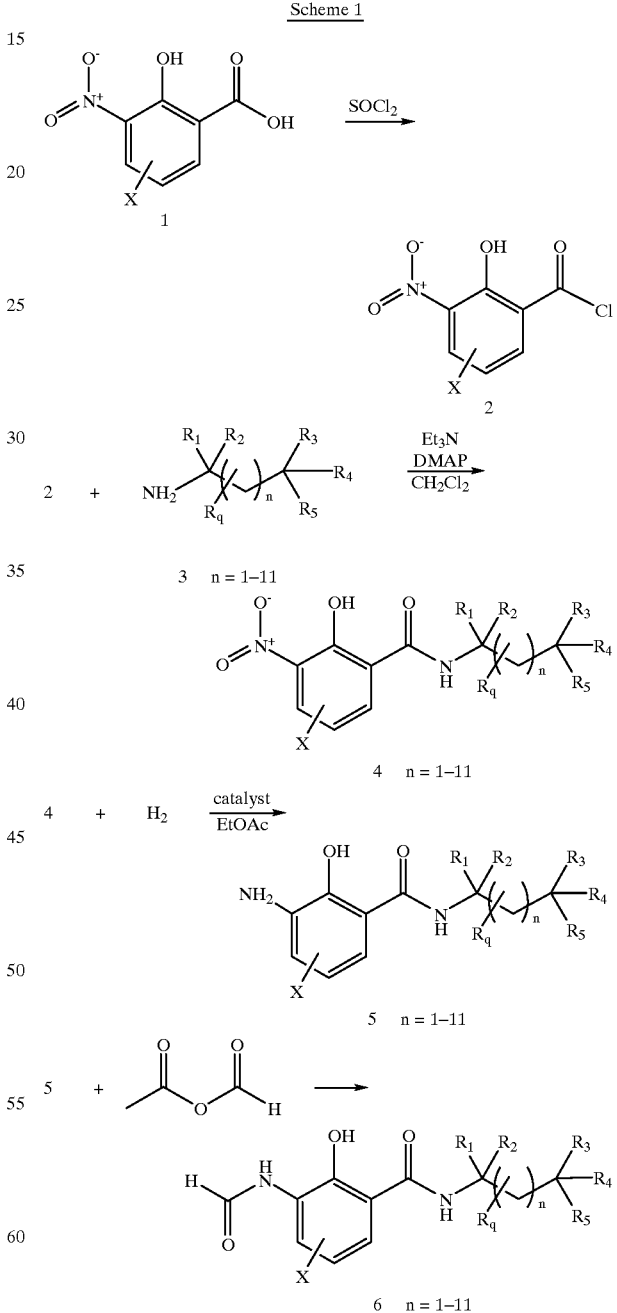

The following discussion presents a description of sample preparations of the AASA compounds of the present invention based upon the foregoing Scheme 1. Throughout this discussion, all temperatures are given in degrees Celsius and all percentages are weight percentages unless otherwise stated.

Obtaining Compound 1

Preparation of 5-Chloro-3-nitrosalicylic Acid

The following procedure demonstrates the preparation of compound 1 with X=5-Cl, with comparable procedures being useful for obtaining related compounds having different X substituents. A solution suspension of 10 g of 5-chlorosalicylic acid in 50 mL glacial acetic acid was cooled in an ice bath until the solvent began to freeze. The bath was exchanged to a room temperature water bath and 4.47 g of 90% fuming nitric acid (1:1 equivalent) in 3 mL glacial acetic acid was added dropwise. After addition was complete, the mixture was stirred for 150 minutes at room temperature (R.T.) in the water bath. It was then poured into 120 mL of ice and water and stirred in an ice bath for 30 minutes. The precipitated solid was collected by filtration and air-dried overnight.

The crude solid was recrystallized from ethanol-water to give 7.86 g of light yellow crystals. This solid was then recrystallized from toluene to give 5.82 g of light yellow needles (m.p. 162–166°).

Converting 1 to 2

Preparation of 2-Hydroxy-3-nitrobenzoyl Chloride

2-Hydroxy-3-nitrobenzoic acid (1, 3-nitrosalicylic acid) was used as obtained from TCI America. A mixture of 3-nitrosalicylic acid (3.46 g), thionyl chloride (10 mL), and N,N-dimethylformamide (3 drops) was stirred and heated at 75° until a homogeneous solution resulted and gas evolution ceased (approximately 20 minutes). Excess thionyl chloride was removed on a rotary evaporator. 1,2-Dichloroethane (30 mL) was added to the yellow residue and the volatiles again removed via rotary evaporation. This was repeated a second time to ensure complete removal of all thionyl chloride. The yellow residual 2-hydroxy-3-nitrobenzoyl chloride (2, X=H) was used immediately in subsequent condensations with amines. The yield was assumed to be quantitative (3.83 g). A similar procedure yields the counterpart products where the 2-hydroxy-3-nitrobenzoic acid has various X substituents.

Preparing the Amine 3

Several different methods were employed to prepare the amine intermediates, depending upon the commercially available starting materials. Some of the amine intermediates were commercially available and did not have to be synthesized. Described below are the various techniques used to arrive at the desired amine intermediate when it was not commercially available.

The procedures described below are typical examples of the general procedures used to prepare the necessary intermediates. They may be easily scaled up or down as needed by one skilled in the art.

Scheme 2

Starting from an Aldehyde

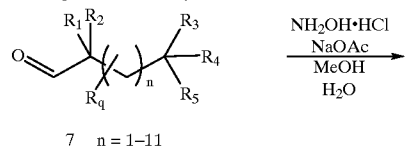

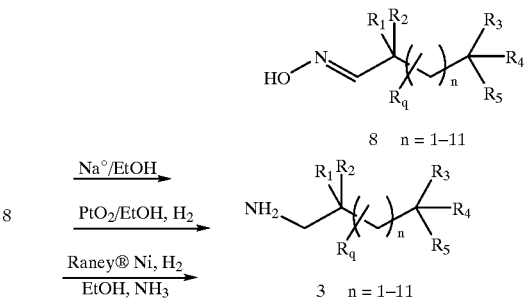

Preparation of several of the requisite amines can be achieved by converting the appropriately substituted aldehyde 7 to the oxime 8 as shown in Scheme 2. Conversion of the oxime 8 to the desired amine 3 can be achieved by use of sodium in boiling ethanol, or catalytically using either platinum oxide or Raney® nickel as a catalyst.

Regardless of the reduction method, the product amines were often obtained as a mixture of isomers. While it was sometimes possible to separate these isomers either at the amine 3 stage (through derivatization or recrystallization of various salts), at the intermediate 3-nitrosalicylamide 4 stage, or at the final AASA product stage, separation was not essential since the final product 6 resulting from each isomer whether in the pure form or in mixtures with other isomers was biologically active.

Preparation of 3,3,7-Trimethyl-oct-6-enaldoxime

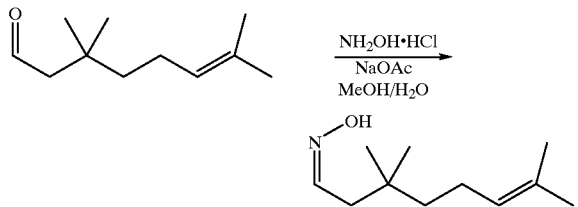

To a stirred solution of 3,3,7-trimethyl-oct-6-enal (1.0 g) in methanol (10 mL) was added all at once a solution of hydroxylamine hydrochloride (1.0 g) and sodium acetate (1.0 g) in water (10 mL). The resulting mixture was heated at reflux for 30 minutes then stirred at room temperature overnight. Water (250 mL) was added and the resulting mixture extracted with pentane (2×100 mL). The pentane extracts were combined, washed with water (2×50 mL), then washed with saturated sodium chloride solution (50 mL). The pentane layer was dried (MgSO$_4$) and the solvent evaporated to give the desired product. Proton NMR (CDCl$_3$) was used to confirm the structure. Analysis by gas chromatography/mass spectroscopy (GC/MS) showed that this material had the correct m/e for the parent ion.

Preparation of 3,3,7-Trimethyl-oct-6-enamine Sodium in Ethanol Method

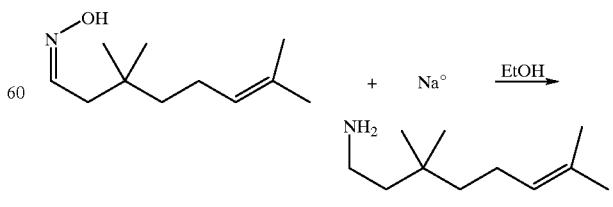

To a solution of 3,3,7-trimethyl-oct-6-enaldoxime (1.10 g) in refluxing ethanol (200 mL) was carefully added over a 30 minute period sodium spheres (approximately 100 g). After the addition was complete, the reaction mixture was heated at reflux until all of the sodium had reacted (about 1 hour). Gas chromatography showed that all of the oxime had reacted and was replaced by a single product. Ice water (400 mL) was carefully added and the resulting mixture extracted with pentane (2×100 mL). The pentane extracts were combined, washed with water (100 mL), then acidified with 1N HCl (100 mL) to pH 1. The layers were separated and the pentane layer was washed with water (50 mL). The water wash and acid layer were combined and washed with pentane (50 mL), then basified with 2N NaOH (approximately 50 mL) to pH 11. The basic solution was extracted with pentane (2×100 mL). The final pentane extracts were combined and washed with water (50 mL), then saturated sodium chloride solution (100 mL), dried (Na$_2$SO$_4$), and the solvent carefully evaporated to give a light yellow oil (1.0 g). Proton NMR (CDCl$_3$) and GC/MS were consistent with this being pure 3,3,7-trimethyl-oct-6-enamine.

Preparation of 3,7-Dimethyl-oct-6-enamine Raney® Nickel Method

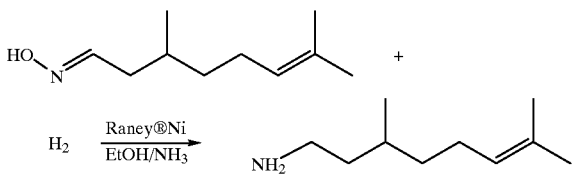

Raney® nickel (3.0 g wet weight) was placed in a 500 mL Parr pressure bottle and was washed with water (3×2 mL) then ethanol (2×2 mL) and finally ethanol saturated with ammonia (1×20 mL), the wash solvent being decanted each time. The ethanol was saturated by bubbling ammonia gas through the solvent for 5 minutes. To the washed catalyst was added a solution of 3,7-dimethyl-oct-6-enaldoxime (3.0 g) in ethanol saturated with ammonia (75 mL). This solution was placed under a hydrogen atmosphere (initial hydrogen pressure=45 psi) on a Parr shaker. After hydrogen uptake ceased (12 hours), gas chromatography showed that the starting oxime was consumed and replaced by a more volatile material. The reaction mixture was filtered, poured into water (350 mL), and extracted with pentane (2×75 mL). The pentane extracts were combined, washed with water (100 mL) then saturated sodium chloride solution (100 mL), dried (Na$_2$SO$_4$), and the solvent evaporated to yield a nearly colorless oil (2.5 g). The proton NMR (CDCl$_3$) and GC/MS were consistent with this being pure 3,7-dimethyl-oct-6-enamine.

Scheme 3

Starting from a Carboxylic Acid

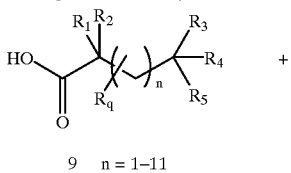

9  n = 1–11

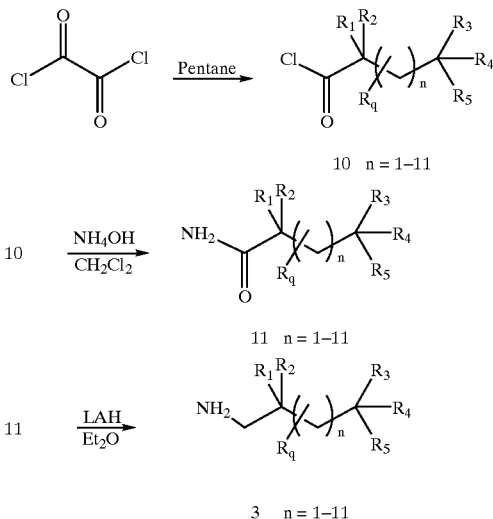

Preparation of some of the desired amines can be achieved by the method described in *J. Labelled Comipd. Rad.*, 23(9), pp.995–1004 (1986), where the appropriately substituted carboxylic acid 9 is converted to the acid chloride 10 and subsequently to the amide 11. Conversion of the amide 11 to the desired amine 3 can be achieved by the method described in *J. Org. Chem.*, 36(14), pp.1968–1971 (1971), where the amide is reduced with lithium aluminum hydride to the desired amine. This general method is depicted above in Scheme 3.

Preparation of 3,5,5-Trimethylhexanamide

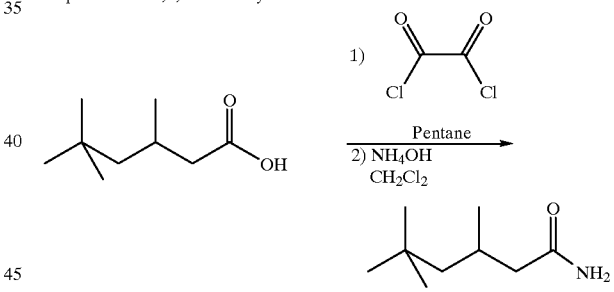

To a stirred solution of 3,5,5-trimethylhexanoic acid (1.12 g) in pentane (30 mL) was added quickly oxalyl chloride (6.2 mL). The mixture was stirred at room temperature until gas evolution ceased (about 2 hours). The mixture was evaporated to a clear oil under vacuum. The oil was dissolved in methylene chloride (50 mL) and stirred vigorously. To the stirred mixture was added a 30% solution of ammonium hydroxide (6 mL) in a slow stream. A white precipitate formed and the mixture was allowed to stir at room temperature overnight. The mixture was evaporated then the resulting slurry was diluted with water (50 mL). The slurry was filtered and the solid washed with ether (100 mL). The combined water and ether filtrates were shaken and then layers separated. The ether layer was washed with water (50 mL) then saturated sodium chloride solution (50 mL), dried (MgSO$_4$), and evaporated to give a white solid (1.2 g). Gas chromatography showed this material to be 97% pure. Proton NMR and direct insertion mass spectroscopy (DI/MS) were consistent with this material being 3,5,5-trimethylhexanamide.

Preparation of 3,5,5-Trimethylhexanamine

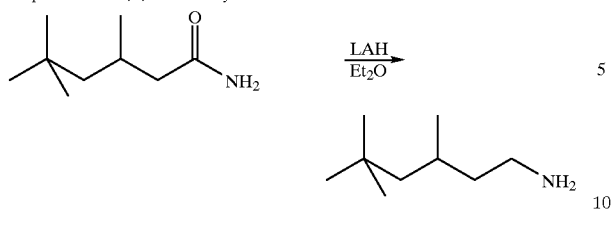

In dry ether (10 mL) under a nitrogen atmosphere lithium aluminum hydride (0.5 g) was suspended with stirring. The suspension was cooled to 0° C. in an ice bath. A solution of 3,5,5-trimethylhexanamide (1.0 g) in dry ether (15 mL) was added to the cooled suspension slowly over about 15 minutes. Gas evolution was evident during the addition. After the addition was complete, the mixture was heated to a gentle reflux overnight. The mixture was cooled to 0° C. in an ice bath and water (0.5 mL) was added slowly. The resultant foaming was allowed to subside and then a 15% solution of sodium hydroxide (0.5 mL) was added slowly followed by water (1.5 mL). The ice bath was removed and the mixture stirred at room temperature for 30 minutes. The salts were filtered and the filtrate evaporated to give a light yellow oil. The oil was taken up in fresh ether (20 mL) and hydrogen chloride gas was bubbled in slowly for 5 minutes. The ether mixture was extracted with water (25 mL) and the ether layer discarded. The aqueous layer was made basic to pH 10 with a 2N solution of sodium hydroxide (about 10 mL) and then extracted with fresh ether (2×25 mL). The combined ether layers were washed with water (10 mL) then a saturated solution of sodium chloride, dried ($Na_2SO_4$), and evaporated to give a clear oil (0.83 g). Gas chromatography showed this to be 98% pure and proton NMR confirmed this material to be 3,5,5-trimethylhexanamine.

Scheme 4

Starting from an Alcohol

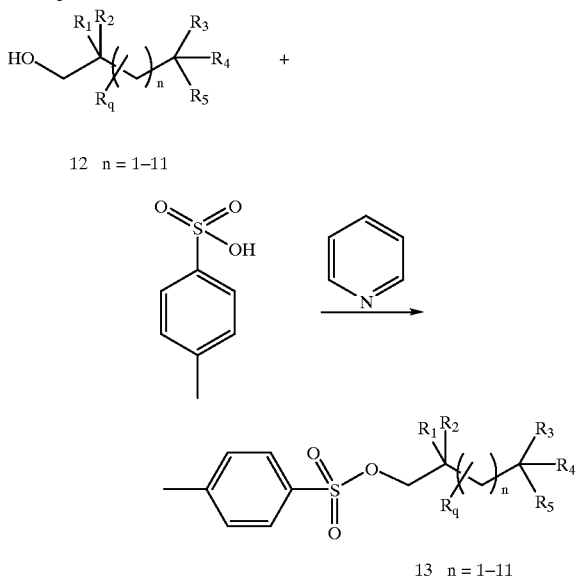

As described above in Scheme 4, preparation of some of the desired amines can be achieved by the method described in *Org. Syn.*, 20, p.50 (1940), where the appropriately substituted alcohol 12 is converted to the tosylate 13. The tosylate can then be converted to the azide 14 by the method described in *J. Org. Chem.*, 61, pp.1650–1654 (1996). Conversion of the azide 14 to the desired amine 3 can be achieved by the method described in *J. Org. Chem.*, 46, pp.4376–4383 (1981), where the azide is reduced with lithium aluminum hydride to the desired amine.

Preparation of 2-isopropyl-5-methyl-O-tosylhexanol

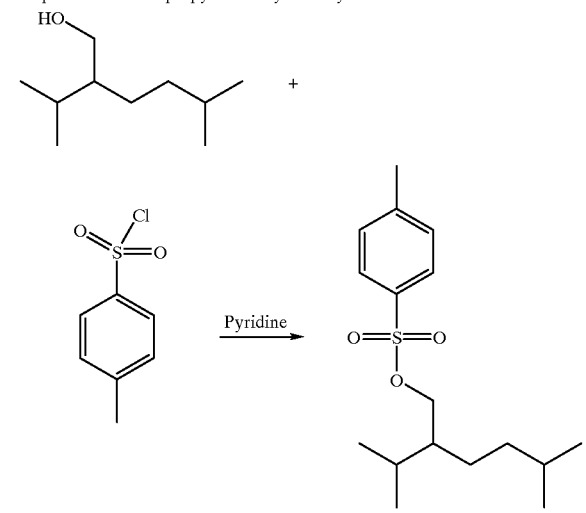

To a solution of 2-isopropyl-5-methylhexanol (2.0 g) in dry pyridine (20 mL) was added para-toluenesulfonyl chloride (2.4 g). The mixture was stirred at room temperature under a nitrogen atmosphere overnight. A white precipitate formed in the reaction mixture. The resulting mixture was diluted with water (250 mL) and then extracted with ether (2×50 mL). The combined ether layers were washed with a 5% copper sulfate solution (2×100 mL) followed by water (100 mL) then a saturated sodium chloride solution (50 mL), dried ($MgSO_4$), and evaporated to yield a clear oil. The crude oil was chromatographed on silica gel using a hexane with 10% acetone mixture as the eluant. A clear oil (3.5 g) was obtained after evaporating the clean fractions. Proton NMR was consistent with this being the pure 2-isopropyl-5-methyl-O-tosylhexanol.

Preparation of 2-isopropyl-5-methylhexyl azide

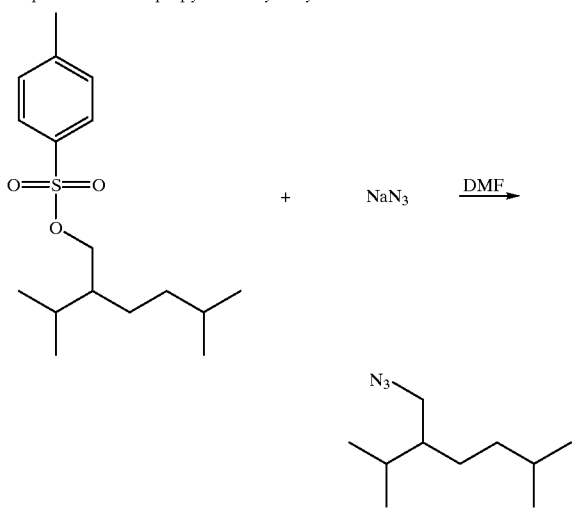

Under a nitrogen atmosphere 2-isopropyl-5-methyl-O-tosylhexanol (3.0 g), sodium azide (31 g), and dimethylformamide (20 mL) were mixed and allowed to stir at room temperature overnight. Gas chromatography revealed approximately 25% starting material remaining. The reaction mixture was heated at 70° C. for 3 hours then allowed to return to room temperature. Gas chromatography showed no evidence of starting material remaining. The reaction mixture was diluted with water (500 mL) and extracted with ether (3×50 mL). The combined ether layers were washed with water (3×50 mL) followed by a saturated sodium chloride solution (50 mL), dried (MgSO$_4$), and evaporated to a clear oil (1.7 g). Gas chromatography showed this oil to be a single product of 98% purity.

Preparation of 2-isopropyl-5-methylhexanamine

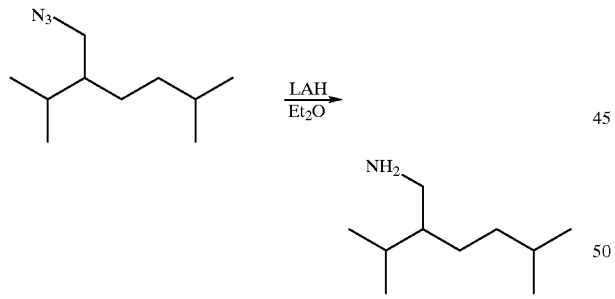

Under a nitrogen atmosphere lithium aluminum hydride (1.14 g) was suspended in dry ether (40 mL) with stirring. A solution of 2-isopropyl-5-methylhexyl azide (1.7 g) in dry ether (20 mL) was slowly added to the slurry over 20 minutes. Vigorous foaming resulted from the addition and after this foaming subsided the mixture was heated to a gentle reflux for 4 hours. The mixture was allowed to return to room temperature and then cooled to 0° C. in an ice bath. Water (1.0 mL) was added slowly and the foaming was allowed to subside then a 15% solution of sodium hydroxide (1 mL) was slowly added followed by water (3 mL). The resulting slurry was stirred at room temperature for 20 minutes then filtered. The filtrate was evaporated to a clear oil (1.5 g). Gas chromatography showed a single product that was 97% pure and proton NMR was consistent with this being 2-isopropyl-5-methylhexanamine.

When the desired amine, aldehyde, carboxylic acid, or alcohol was not available, standard methods described in the chemical literature were employed to derivative various starting materials and arrive at the desired amine. Useful procedures were found in D. L. J. Clive, V. Farina, and P. L. Beaulieu, *J. Org. Chem.*, 47(13), pp. 2572–2582 (1982); H. O. House and H. W. Thompson, *J. Org. Chem.*, 26, pp. 3729–3734 (1961); P. Dampawan and W. W. Zajac, *Synthesis*, pp. 545–546 (1983); R. Ballini and M. Petrini, *Syn. Comm.*, 16(14), pp. 1781–1788 (1986); K. Steliou and M. Poupart, *J. Org. Chem.*, 50(24), pp. 4971–4974 (1985); and Huang-Minlon, *J. Am. Chem. Soc.*, 68, pp. 2487–2488 (1946). Useful intermediates were compounds such as citral and 3,3,5,5-tetramethylcyclohexanone which are commercially available. Anyone skilled in the art could use similar procedures to build up various derivatized amines.

The foregoing methods were used to prepare the respective amines required for preparation of the final AASA products hereafter described. Included among the prepared amines are the following novel amines described in Table 1:

TABLE 1

| | Novel Amines | | |
|---|---|---|---|
| Compound Number | Appearance | Molecular Ion (M) | Structure |
| 1 | yellow oil | 169 | |
| 2 | clear oil | 157 | |
| 3 | yellow oil | 157 | |

TABLE 1-continued

Novel Amines

| Compound Number | Appearance | Molecular Ion (M) | Structure |
|---|---|---|---|
| 4 | clear oil | 143 | 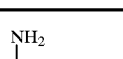 |

Preparing the 3-Nitrosalicylamide

Preparation of N-(3,3,7-trimethyl-oct-6-enyl)-2-hydroxy-3-nitrobenzamide

To a stirred solution of 3,3,7-trimethyl-oct-6-enamine (1.0 g), triethylamine (1.0 g), and 4-dimethylaminopyridine (50 mg) in dichloromethane (50 mL) was added, in a rapid dropwise manner, a solution of 2-hydroxy-3-nitrobenzoyl chloride (1.2 g) in dichloromethane (50 mL). After the addition was complete, the reaction mixture was stirred at room temperature for 12 hours, then poured into 1N solution of hydrochloric acid (10 mL). The layers were separated and the organic layer washed a second time with 1N solution of hydrochloric acid (50 mL) followed by water (100 mL) then a saturated sodium chloride solution (50 mL), dried (MgSO$_4$), and evaporated to give a yellow oil (2.0 g). The crude oil was chromatographed on silica gel using a mixture of hexane, 19.8% acetone, and 0.2% acetic acid as the eluant. The clean fractions were combined and evaporated to get a yellow solid (1.0 g). Proton NMR and DI/MS were consistent with pure N-(3,3,7-trimethyl-oct-6-enyl)-2-hydroxy-3-nitrobenzamide.

The foregoing procedure was used with corresponding amines to prepare the 3-nitrosalicylamides described in the following Tables 2 and 3:

TABLE 2

3-Nitrosalicylamide Intermediates

| Compound Number | Molecular Ion (M) | Structure |
|---|---|---|
| 101 | 383 | 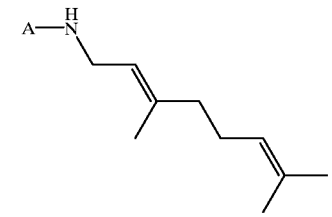 |
| 102 | | 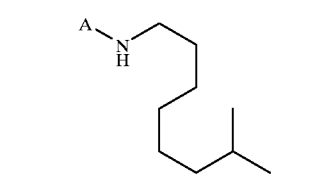 |
| 103 | M + H 319 | 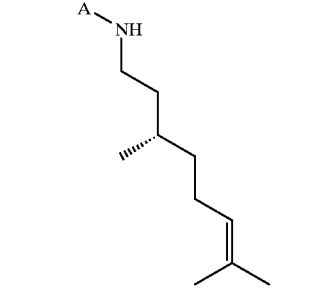 |
| 104 | 309 | 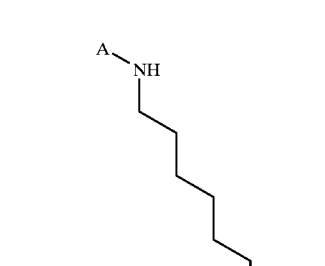 |
| 105 | M + H 321 | 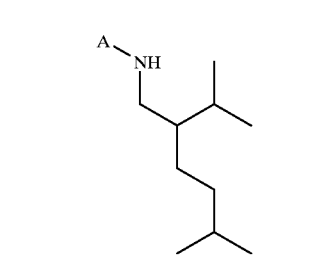 |
| 106 | M + H 281 | 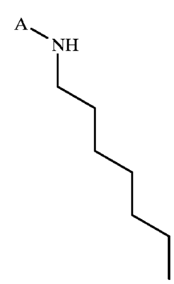 |
| 107 | M − H 321 | 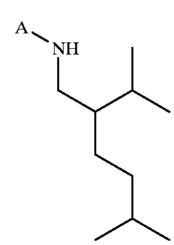 |

TABLE 2-continued
3-Nitrosalicylamide Intermediates
| Compound Number | Molecular Ion (M) | Structure |
|---|---|---|
| 108 | M − H 293 | 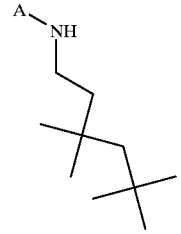 |
| 109 | M + H 295 | 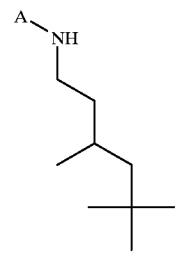 |
| 110 | M + H 323 | 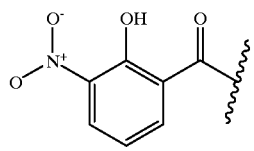 |
| 111 | M + H 309 | 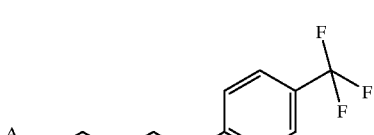 |
Note: In the Structure column in the Table, A =
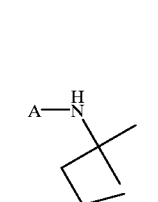
TABLE 3
3-Nitrosalicylamide Intermediates
Activity & Structure Table
In Vivo Testing
| Compound Number | PLASVI (GDM) | PHYTIN (LBT) | ERYSGT (PMW) | PUCCRT (LRW) | LEPTNO (SNW) | PYRIOR | Structure |
|---|---|---|---|---|---|---|---|
| 101 | ++ | + | | | | | 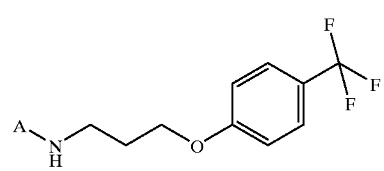 |
| 102 | + | | ++ | + | | ++ | 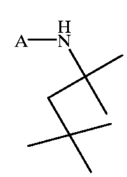 |

TABLE 3-continued
3-Nitrosalicylamide Intermediates
Activity & Structure Table
In Vivo Testing
| Compound Number | PLASVI (GDM) | PHYTIN (LBT) | ERYSGT (PMW) | PUCCRT (LRW) | LEPTNO (SNW) | PYRIOR | Structure |
|---|---|---|---|---|---|---|---|
| 103 | − | | ++ | − | − | + | 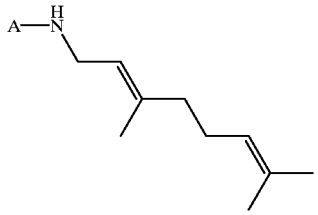 |
| 104 | | + | + | ++ | | | 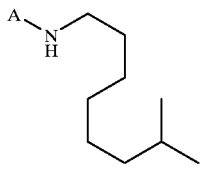 |
| 105 | − | − | − | + | | | 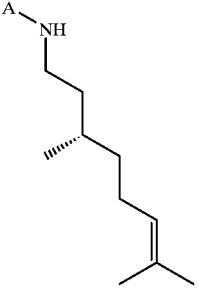 |
| 106 | | − | − | + | − | | 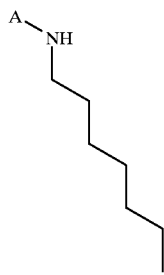 |
| 107 | | − | − | + | − | | 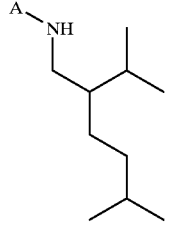 |

TABLE 3-continued
3-Nitrosalicylamide Intermediates
Activity & Structure Table
In Vivo Testing
| Compound Number | PLASVI (GDM) | PHYTIN (LBT) | ERYSGT (PMW) | PUCCRT (LRW) | LEPTNO (SNW) | PYRIOR | Structure |
|---|---|---|---|---|---|---|---|
| 108 | | − | − | ++ | − | | 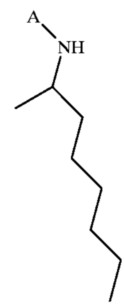 |
| 109 | | + | − | − | − | | 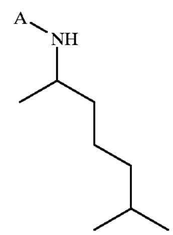 |
| 110 | | − | − | ++ | − | | 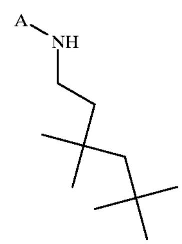 |
| 111 | | − | + | − | − | | 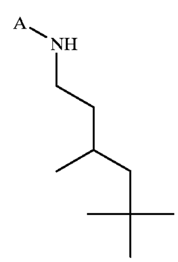 |
Rate = 100 ppm
Scale:
blank space = not tested
− = 0–29% disease control
+ = 30–74% disease control
++ = 75–100% disease control
Note: In the Structure column in the Table, the A =
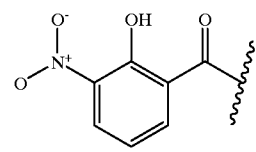

Preparing the AASA Compound 6

Preparation of 3-Formamido-2-hydroxy-N-(3,3,7-trimethyl-oct-6-enyl)-benzamide

To a solution of N-(3,3,7-trimethyl-oct-6-enyl)-2-hydroxy-3-nitrobenzamide (0.9 g) in ethyl acetate (75 mL) was added 5% Pd/C (0.2 g) catalyst. The resulting mixture was subjected to a hydrogen atmosphere (initial $H_2$ pressure=45 psi) using a Parr shaker apparatus. When hydrogen uptake ceased (approximately 1 hour), the hydrogen atmosphere was purged and replaced with nitrogen. A stir bar was added to the reaction bottle and to the stirred reaction mixture acetic formic anhydride (1.5 mL) was added all at once. After stirring at room temperature for 30 minutes, the reaction mixture was filtered, washed with a saturated sodium bicarbonate solution (2×100 mL), then water (100 mL), and finally a saturated sodium chloride solution (50 mL), dried ($MgSO_4$), and evaporated to give a light brown oil (0.9 g). Proton NMR and DI/MS were consistent with this being pure 3-formamido-2-hydroxy-N-(3,3,7-trimethyl-oct-6-enyl)-benzamide.

Based upon the foregoing preparations and utilizing the corresponding 3-nitrosalicylamides, the following acylated aminosalicylamides listed in Table 4 were prepared.

TABLE 4

| Compound Number | Melting Point (° C.) | Molecular Ion (M) | Structure |
|---|---|---|---|
| 201 | | | |
| 202 | 110–114 | | |
| 203 | | 316 | |
| 204 | | M + H 321 | |
| 205 | | M + H 306 | 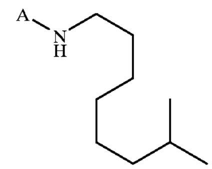 |
| 206 | | M + H 237 | 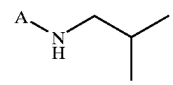 |
| 207 | | M + H 234 | 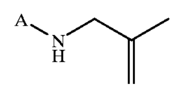 |
| | | | (mixture) |
| 208 | | M + H 319 | 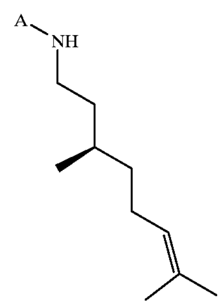 |
| 209 | | M + H 319 | 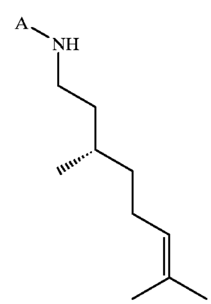 |
| 210 | | 278 | 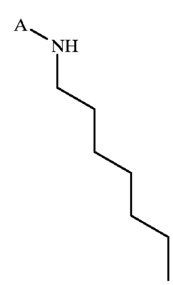 |

TABLE 4-continued
| Compound Number | Melting Point (° C.) | Molecular Ion (M) | Structure |
|---|---|---|---|
| 211 | | 292 | 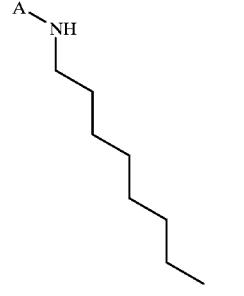 |
| 212 | | M + H 321 | 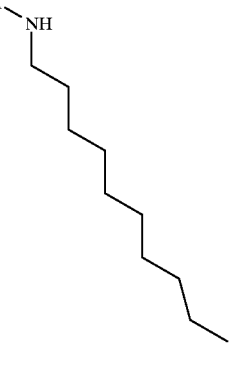 |
| 213 | | M − H 361 | 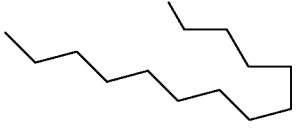 |
| 214 | | 332 | 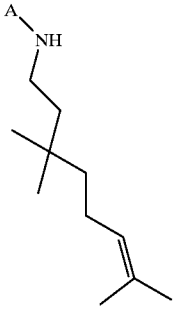 |
| 215 | | 320 | 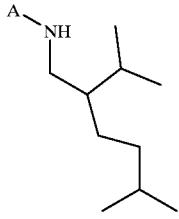 |
| 216 | | M + H 251 | 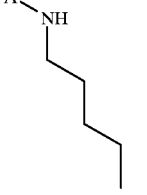 |
| 217 | | M + H 265 | 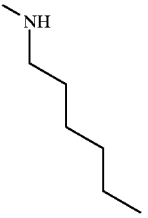 |
| 218 | | M + H 279 | 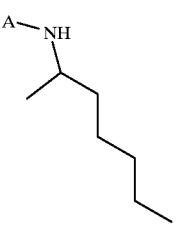 |
| 219 | | 292 | 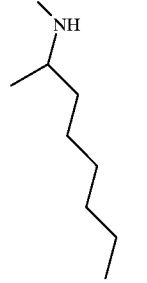 |
| 220 | | 292 | 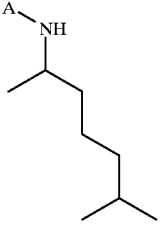 |
| 221 | | 320 | 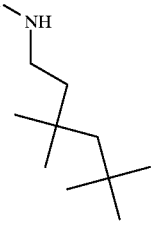 |

TABLE 4-continued

| Compound Number | Melting Point (° C.) | Molecular Ion (M) | Structure |
|---|---|---|---|
| 222 | | M + H 307 | 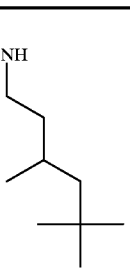 |

Note: In the Structure column in the Table, the A =

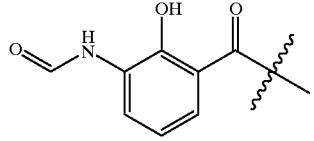

Fungicide Utility

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion. The compounds of the invention may also be used to protect stored grain, wood products and other non-plant loci from fungal infestation.

The AASA compounds of Formula I show strong fungicidal activity against a wide variety of fungi. The following tests were performed in the laboratory and illustrate the fungicidal efficacy of the compounds of the invention. The following protocols are established and understood by those in the art as evidencing the utility of the compounds for the purposes indicated.

Compound formulation was accomplished by dissolving technical materials in acetone, with serial dilutions then made in acetone to obtain desired concentrations. Final treatment volumes were obtained by adding nine volumes 0.05% aqueous Tween-20 or 0.01% Triton X-100, depending upon the pathogen.

Downy Mildew of Grape (*Plasmopara viticola*—PLASVI) (24 Hour Protectant): Vines (cultivar Carignane) were grown from seed in a soilless peatbased potting mixture ("Metromix") until the seedlings were 10–20 cm tall. These plants were then sprayed to run off with the test compound at a rate of 100 ppm. After 24 hours the test plants were inoculated by spraying with an aqueous sporangia suspension of *Plasmopara viticola*. The plants were then transferred to the greenhouse until disease developed on the untreated control plants.

Late Blight of Tomato (*Phytophthora infestans*—PHYTIN): Tomatoes (cultivar Rutgers) were grown from seed in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous sporangia suspension of *Phytophthora infestans*. The plants were then transferred to the greenhouse until disease developed on the untreated control plants.

Powdery Mildew of Wheat (*Erysiphe graminis*—ERYSGT): Wheat (cultivar Monon) was grown in a soilless peat-based potting mixture ("Metromix") until the seedlings were 10–20 cm tall. The plants were sprayed to run off with the test compound at a rate of 100 ppm. After 24 hours, these plants were inoculated with *Erysiphe graminis* by dusting spores from stock plants onto the test plants. The test plants were kept in the greenhouse until disease developed on the untreated control plants.

Brown rust of Wheat (*Puccinia recondita*—PUCCRT): Wheat (cultivar Monon) was grown in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous spore suspension of *Puccinia recondita*. The plants were then transferred to the greenhouse until disease developed on the untreated control plants.

Leaf Blotch of Wheat (*Septoria tritici*—SEPTTR): Wheat (cultivar Monon) was grown in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous spore suspension of *Septoria tritici*. The plants were then transferred to the greenhouse until disease developed on the untreated control plants.

Glume Blotch of Wheat (*Septoria nodorum*—LEPTNO): Wheat (cultivar Monon) was grown in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous spore suspension of *Septoria nodorum*. The plants were then transferred to the greenhouse until disease developed on the untreated control plants.

Rice Blast (*Pyricularia orvzae*—PYRIOR): Rice (cultivar M9) was grown from seed in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous suspension of *Pyricularia oryzae* conidia. The plants were then transferred to the greenhouse until disease developed on the untreated control plants.

Apple Scab (*Venturia inaegualis*—VENTIN): Apples (cultivar Red Delicious) were grown from seed in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous suspension of *Venturia inaequalis* spores. The plants were then transferred to the greenhouse until disease developed on the untreated control plants.

Wood Decay Fungi—In Vitro methods: Cultures of wood *Gloeophyllum trabeum* (LENZTR) and *Trametes versicolor* (CORLVE) are grown by submerged static culture in Potato Dextrose—0.5% Yeast Extract (PDY) broth for approximately 7 days prior to use at room temperature. Cultures of *Postia placenta* (POSTPL) and *Trametes lilacino-gilva* (TRAMLI) are similarly grown except that Bacto™ YM broth is used instead of PDY. *Chaetomium globosum* (CHATGL) is grown by submerged static culture in Malt Extract broth at 24–25° C. Mycelia are harvested by filtration, re-suspended in fresh broth, and fragmented using sterilized stainless steel blender cups. Prior to inoculating plates, inoculum suspensions are adjusted with additional broth to a standard concentration determined by optical density. Test compounds are dissolved in DMSO and added to 96 well microtiter plates. Two-hundred μl of inoculum-broth are added to each well. Percent inhibition is determined by comparing growth in treated wells after 2–3 days to growth in solvent blank wells.

The following tables present the activity of typical compounds of the present invention when evaluated in the referenced experiments. The test compounds were used at a rate of 100 ppm. The effectiveness of the test compounds in controlling disease was rated using the scale shown in the Key on the Tables 5 and 6.

TABLE 5

Activity & Structure Table
In Vivo Testing

| Compound Number | PLASVI (GDM) | PHYTIN (LBT) | ERYSGT (PMW) | PUCCRT (LRW) | SEPTTR (STW) | LEPTNO (SNW) | PYRIOR | VENTIN | Structure |
|---|---|---|---|---|---|---|---|---|---|
| 201 | ++ | ++ | | | | | | | 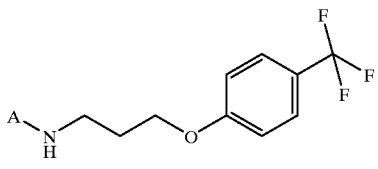 |
| 202 | ++ | ++ | + | ++ | | ++ | ++ | + | 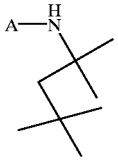 |
| 203 | ++ | ++ | − | + | | ++ | + | | 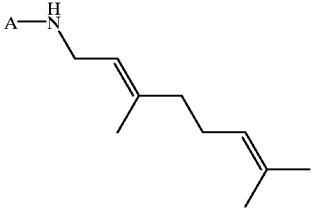 |
| 204 | ++ | ++ | − | + | + | ++ | + | ++ | 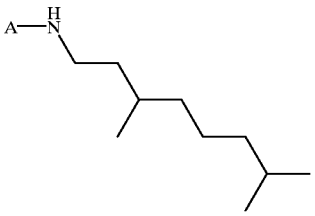 |
| 205 | ++ | ++ | + | ++ | + | | | | 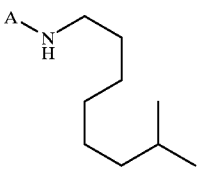 |
| 206 | + | − | + | − | | + | | | 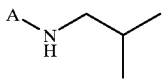 |
| 207 | + | − | − | − | | − | | | 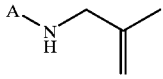 |

TABLE 5-continued
Activity & Structure Table
In Vivo Testing
| Compound Number | PLASVI (GDM) | PHYTIN (LBT) | ERYSGT (PMW) | PUCCRT (LRW) | SEPTTR (STW) | LEPTNO (SNW) | PYRIOR | VENTIN | Structure |
|---|---|---|---|---|---|---|---|---|---|
| | | | | | | | | | 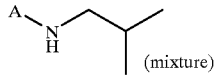 (mixture) |
| 208 | ++ | ++ | + | ++ | | − | | | 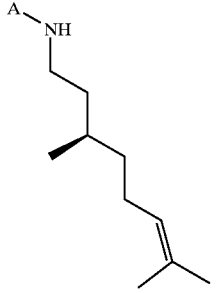 |
| 209 | ++ | ++ | − | + | | + | | | 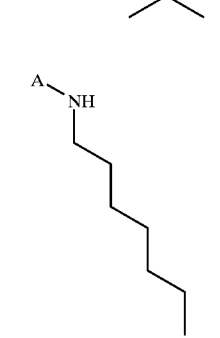 |
| 210 | ++ | ++ | + | ++ | − | ++ | | | 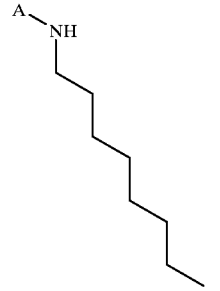 |
| 211 | ++ | ++ | − | − | − | ++ | | | 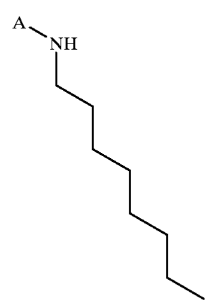 |

TABLE 5-continued
Activity & Structure Table
In Vivo Testing
| Compound Number | PLASVI (GDM) | PHYTIN (LBT) | ERYSGT (PMW) | PUCCRT (LRW) | SEPTTR (STW) | LEPTNO (SNW) | PYRIOR | VEN-TIN | Structure |
|---|---|---|---|---|---|---|---|---|---|
| 212 | ++ | + | + | − | − | ++ | | | 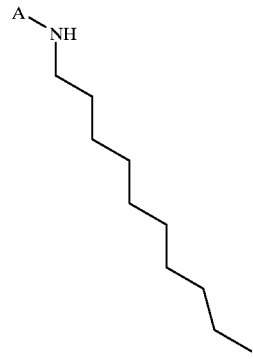 |
| 213 | + | + | − | − | − | + | | | 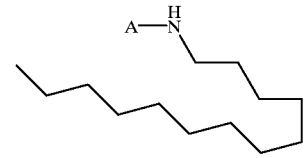 |
| 214 | ++ | ++ | − | − | + | ++ | | | 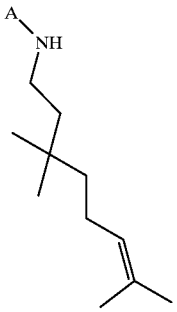 |
| 215 | ++ | ++ | + | ++ | − | ++ | | | 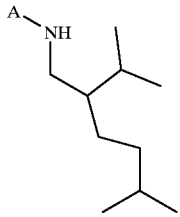 |
| 216 | + | − | − | + | − | ++ | | | 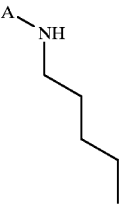 |

TABLE 5-continued

Activity & Structure Table
In Vivo Testing

| Compound Number | PLASVI (GDM) | PHYTIN (LBT) | ERYSGT (PMW) | PUCCRT (LRW) | SEPTTR (STW) | LEPTNO (SNW) | PYRIOR | VENTIN | Structure |
|---|---|---|---|---|---|---|---|---|---|
| 217 | ++ | − | − | − | + | − | | | 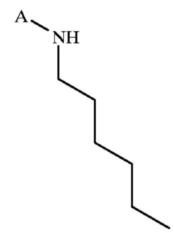 |
| 218 | ++ | + | − | ++ | − | ++ | | | 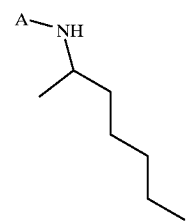 |
| 219 | ++ | ++ | − | ++ | − | ++ | | | 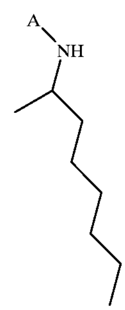 |
| 220 | ++ | ++ | − | ++ | | ++ | | | 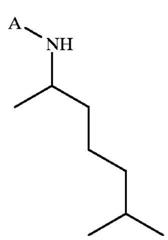 |
| 221 | ++ | ++ | − | ++ | | ++ | | | 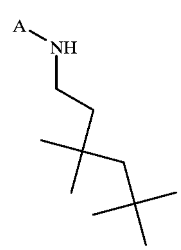 |

TABLE 5-continued

Activity & Structure Table
In Vivo Testing

| Compound Number | PLASVI (GDM) | PHYTIN (LBT) | ERYSGT (PMW) | PUCCRT (LRW) | SEPTTR (STW) | LEPTNO (SNW) | PYRIOR | VENTIN | Structure |
|---|---|---|---|---|---|---|---|---|---|
| 222 | ++ | ++ | − | ++ | + | ++ | | | 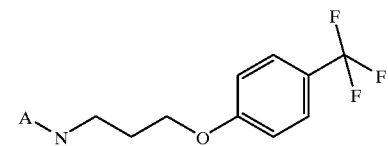 |

Rate = 100 ppm
Scale:
blank space = not tested
− = 0–29% disease control
+ = 30–74% disease control
++ = 75–100% disease control
In the Structure column, A =

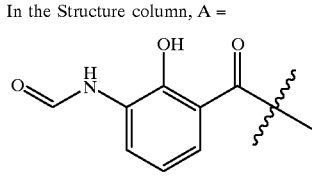

TABLE 6

Activity & Structure Table
In Vitro Testing

| Compound Number | CORLVE | LENZTR | TRAMLI | POSTPL | CHATGL | Structure |
|---|---|---|---|---|---|---|
| 201 | + | ++ | + | ++ | ++ | 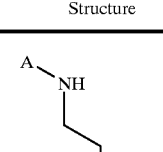 |
| 202 | − | + | − | − | + | 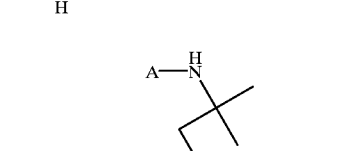 |
| 203 | + | + | − | − | − | 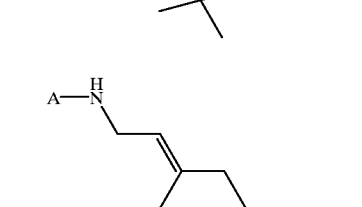 |

TABLE 6-continued
Activity & Structure Table
In Vitro Testing
| Compound Number | CORLVE | LENZTR | TRAMLI | POSTPL | CHATGL | Structure |
|---|---|---|---|---|---|---|
| 204 | + | ++ | − | + | − | 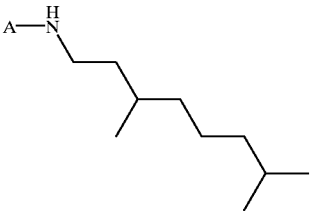 |
| 205 | + | ++ | + | + | + | 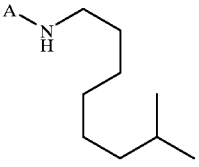 |
| 206 | + | + | − | + | + | 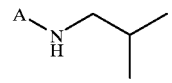 |
| 207 | + | + | − | − | − |  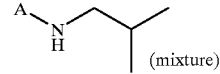 (mixture) |
| 208 | + | + | − | − | − | 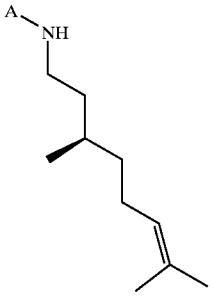 |

TABLE 6-continued

Activity & Structure Table
In Vitro Testing

| Compound Number | CORLVE | LENZTR | TRAMLI | POSTPL | CHATGL | Structure |
|---|---|---|---|---|---|---|
| 209 | + | ++ | + | − | − | 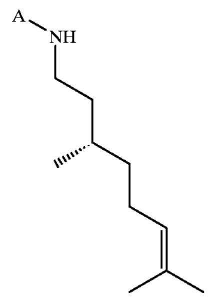 |
| 210 | + | + | − | − | + | 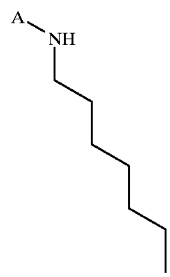 |
| 211 | + | + | − | + | − | 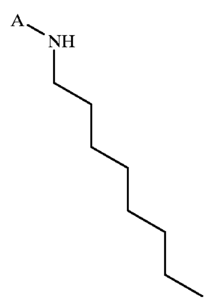 |
| 212 | + | + | − | + | − | 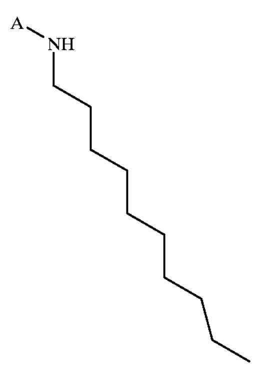 |
| 213 | + | + | − | + | − | 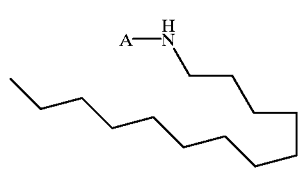 |

TABLE 6-continued

Activity & Structure Table
In Vitro Testing

| Compound Number | CORLVE | LENZTR | TRAMLI | POSTPL | CHATGL | Structure |
|---|---|---|---|---|---|---|
| 214 | + | + | + | + | + | 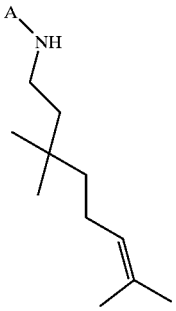 |

Rate = 1 ppm
Scale:
blank space = not tested
− = 0–29% disease control
+ = 30–74% disease control
++ = 75–100% disease control
In the Structure column, A =

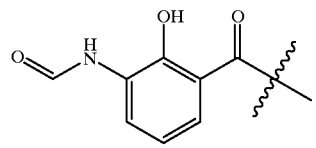

While the invention has been illustrated and described in detail in the foregoing description, the same is to be considered illustrative and not restrictive in character, it being understood that only the preferred embodiment has been described and that all changes and modifications that come within the spirit of the invention are desired to be protected.

What is claimed is:

1. The acylated aminosalicylamide compound of the Formula I:

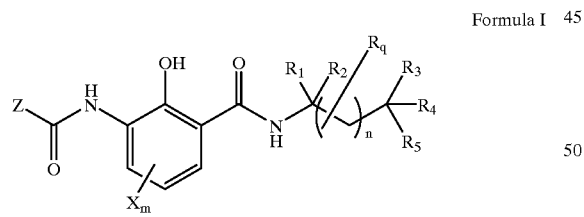

Formula I wherein:
a. m is 1 or 2;
b. ( )n represents a carbon chain including "n" number of carbon atoms where n is 1 to 11;
c. q is from 0 to 2n;
d. each X is independently selected from the group consisting of H, halogen, $C_1$–$C_4$ alkyl, $C_2$–$C_4$ alkenyl, cyclopropyl, cyano, $NO_2$, $C_1$–$C_4$ haloalkyl, hydroxy, $C_1$–$C_3$ alkoxy, $C_1$–$C_3$ haloalkoxy, $C_1$–$C_3$ alkylthio, $C_1$–$C_3$ alkylsulfonyl, $C_1$–$C_3$ alkylsulfinyl, $C_1$–$C_2$ SCOalkyl, $C_1$–$C_3$ NHalkyl, $C_1$–$C_3$ N(alkyl)$_2$, $C_1$–$C_3$ NHCOalkyl, NHC(O)H, $C_1$–$C_3$ N-alkyl COalkyl, $C_1$–$C_3$ NHCONHalkyl, $C_1$–$C_2$ NHCON(alkyl)$_2$, NHC(O)$R_x$, C(O)$R_x$, C(O)O$R_x$, and C(O)N$R_x$$R_x$, in which $R_x$ is independently H or $C_1$–$C_4$ alkyl;
e. Z is selected from the group consisting of H, $C_1$–$C_2$ alkyl, $CH_3NH$ and $Me_2N$;
f. $R_1$ and $R_2$ may be the same or different, but at least one of $R_1$ and $R_2$ must be H or methyl, and each of $R_1$ and $R_2$ is independently selected from the group consisting of H, cyano, $C_1$–$C_4$ alkyl (straight chain or branched), $C_2$–$C_4$ alkenyl (straight chain or branched), aryl, $C_1$–$C_4$ haloalkyl (straight chain or branched), $C_1$–$C_4$ carboalkoxy optionally substituted with one or more of $OR_6$, $SR_6$, $NR_6R_7$, halogen or cyano;
g. $R_3$, $R_4$, and $R_5$ may be the same or different and each of $R_3$–$R_5$ is independently selected from the group consisting of H, halogen, $C_1$–$C_3$ alkoxy, $C_1$–$C_3$ haloalkoxy, $C_3$–$C_6$ cycloalkoxy, aryloxy, C(=O)$R_6$ and C(=O)O$R_6$;
h. each $R_q$ can be the same or different and each $R_q$ is defined as follows:
  i. any or all of $R_q$ are selected from the group consisting of H, halogen, cyano, $C_1$–$C_4$ alkyl (straight chain or branched), $C_2$–$C_4$ alkenyl (straight chain or branched), aryl, $C_1$–$C_4$ haloalkyl (straight chain or branched), $C_1$–$C_4$ alkoxy (straight chain or branched), $C_1$–$C_4$ haloalkoxy (straight chain or branched), $C_1$–$C_4$ carboalkoxy, and $C_3$–$C_6$ cycloalkyl optionally substituted with one or more of $OR_6$ $SR_6$, $NR_6R_7$, halogen or cyano;
  ii. any of $R_q$ can be hydroxy provided that no two geminal $R_q$ are both hydroxy;
  iii. any adjacent $R_q$ can be combined as unsaturations in the main chain to form alkenyl or alkynyl bonds as allowed by chemical bonding rules; and iv. any of geminal $R_q$ can be combined in a double bond to an oxygen;
i. the number of substituents included as $R_q$ will vary depending on n and q in accordance with chemical bonding rules;
j. $R_6$ and $R_7$ may be the same or different and each of $R_6$ and $R_7$ is selected from the group consisting of H, $C_1$–$C_4$ alkyl, $C_3$–$C_4$ alkenyl, $C_3$–$C_4$ alkynyl, $C_3$–$C_6$ cycloalkyl, aryl and $C_1$–$C_4$ alkoxyalkyl, except that $R_7$ can not be H;
k. aryl, as used herein, may be unsubstituted or may have up to three substituents selected from the group consisting of halogen, $C_1$–$C_4$ alkyl, $C_2$–$C_4$ alkenyl, $C_3$–$C_6$ cycloalkyl, cyano, $C_1$–$C_4$ haloalkyl, hydroxy, $C_1$–$C_3$ alkoxy, $C_1$–$C_3$ haloalkoxy and aryloxy; and
l. when stereocenters are formed by various substitution patterns as described herein, all isomers are included in the definitions for the structure of Formula I, said acylated aminosalicylamides however not including L-Glutamic acid, N-[3-(formylamino)-2-hydroxybenzoyl]-, dipropyl ester; L-Glutamic acid, N-[3-(formylamino)-2-hydroxybenzoyl]-, dibutyl ester; L-Aspartic acid, N-[3-(formylamino)-2-hydroxybenzoyl]-, bis(2,2-dimethylpropyl) ester; Benzamide, 3-(formylamino)-2-hydroxy-N-pentyl-; Benzamide, 3-(formylamino)-2-hydroxy-N-butyl-; Benzamide, 3-(formylamino)-2-hydroxy-N-octyl-; Benzamide, 3-(formylamino)-2-hydroxy-N-decyl-; Benzamide, 3-(formylamino)-2-hydroxy-N-dodecyl-; Benzamide, 3-(formylamino)-2-hydroxy-N-hexyl-.

2. The compound of claim 1 in which Z is H.
3. The compound of claim 1 in which each X is H or 5-fluoro.
4. The compound of claim 3 in which Z is H.
5. The compound of claim 1 in which each of $R_1$–$R_5$ is H.
6. The compound of claim 5 in which Z is H.
7. The compound of claim 5 in which each X is H or 5-fluoro.
8. The compound of claim 7 in which Z is H.
9. The compound of claim 1 in which at least one of $R_1$ and $R_2$ is other than hydrogen.
10. The compound of claim 9 in which Z is H.
11. The compound of claim 9 in which each X is H or 5-fluoro.
12. The compound of claim 11 in which Z is H.
13. The compound of claim 1 in which there are 1–4 $R_q$'s other than hydrogen and all of $R_{3-5}$ are hydrogen.
14. The compound of claim 13 in which Z is H.
15. The compound of claim 13 in which each X is H or 5-fluoro.
16. The compound of claim 15 in which Z is H.
17. The compound of claim 13 in which at least one of $R_1$ and $R_2$ is other than hydrogen.
18. The compound of claim 1 in which n is 4–6.
19. The compound of claim 18 in which Z is H.
20. The compound of claim 18 in which each X is H or 5-fluoro.
21. The compound of claim 20 in which Z is H.
22. The compound of claim 18 in which each of $R_1$–$R_5$ is H.
23. The compound of claim 18 in which there are 1–4 $R_q$'s which are other than hydrogen and all of $R_{3-5}$ are hydrogen.
24. The compound of claim 18 in which at least two of $R_{3-5}$ is other than hydrogen.
25. The compound of claim 24 in which at least one of $R_1$ and $R_2$ is other than hydrogen.
26. The compound of claim 25 in which Z is H.
27. The compound of claim 25 in which each X is H or 5-fluoro.
28. The compound of claim 27 in which Z is H.
29. A fungicidal composition comprising the compound of claim 1 and a phytologically acceptable carrier.
30. The composition of claim 29 and which further includes at least one other compound selected from the group consisting of insecticides, fungicides, herbicides, nematocides, miticides, arthropodicides, bactericides and combinations thereof.
31. A method for the control or prevention of fungal infestation, which method comprises applying to the locus of the fungus, or the locus in which the infestation is to be controlled or prevented, a fungicidally effective amount of an acylated aminosalicylamide compound of the Formula I:

Formula I wherein:
a. m is 1 or 2;
b. ( )n represents a carbon chain including "n" number of carbon atoms where n is 1 to 11;
c. q is from 0 to 2n;
d. each X is independently selected from the group consisting of H, halogen, $C_1$–$C_4$ alkyl, $C_2$–$C_4$ alkenyl, cyclopropyl, cyano, $NO_2$, $C_1$–$C_4$ haloalkyl, hydroxy, $C_1$–$C_3$ alkoxy, $C_1$–$C_3$ haloalkoxy, $C_1$–$C_3$ alkylthio, $C_1$–$C_3$ alkylsulfonyl, $C_1$–$C_3$ alkylsulfinyl, $C_1$–$C_2$ SCOalkyl, $C_1$–$C_3$ NHalkyl, $C_1$–$C_3$ N(alkyl)$_2$, $C_1$–$C_3$ NHCOalkyl, NHC(O)H, $C_1$–$C_3$ N-alkyl COalkyl, $C_1$–$C_3$ NHCONHalkyl, $C_1$–$C_2$ NHCON(alkyl)$_2$, NHC(O)$R_x$, C(O)$R_x$, C(O)O$R_x$, and C(O)N$R_x R_x$, in which $R_x$ is independently H or $C_1$–$C_4$ alkyl;
e. Z is selected from the group consisting of H, $C_1$–$C_2$ alkyl, $CH_3NH$ and $Me_2N$;
f. $R_1$ and $R_2$ may be the same or different, but at least one of $R_1$ and $R_2$ must be H or methyl, and each of $R_1$ and $R_2$ is independently selected from the group consisting of H, cyano, $C_1$–$C_4$ alkyl (straight chain or branched), $C_2$–$C_4$ alkenyl (straight chain or branched), aryl, $C_1$–$C_4$ haloalkyl (straight chain or branched), $C_1$–$C_4$ carboalkoxy optionally substituted with one or more of $OR_6$, $SR_6$, $NR_6R_7$, halogen or cyano;
g. $R_3$, $R_4$, and $R_5$ may be the same or different and each of $R_{3-5}$ is independently selected from the group consisting of H, halogen, $C_1$–$C_3$ alkoxy, $C_1$–$C_3$ haloalkoxy, $C_3$–$C_6$ cycloalkoxy, aryloxy, C(=O)$R_6$ and C(=O)O$R_6$;
h. each $R_q$ can be the same or different and each $R_q$ is defined as follows:
i. any or all of $R_q$ are selected from the group consisting of H, halogen, cyano, $C_1$–$C_4$ alkyl (straight chain or branched), $C_2$–$C_4$ alkenyl (straight chain or branched), aryl, $C_1$–$C_4$ haloalkyl (straight chain or branched), $C_1$–$C_4$ alkoxy (straight chain or branched), $C_1$–$C_4$ haloalkoxy (straight chain or branched), $C_1$–$C_4$ carboalkoxy, and $C_3$–$C_6$ cycloalkyl optionally substituted with one or more of $OR_6$ $SR_6$, $NR_6R_7$, halogen or cyano;

ii. any of $R_q$ can be hydroxy provided that no two geminal $R_q$ are both hydroxy;

iii. any adjacent $R_q$ can be combined as unsaturations in the main chain to form alkenyl or alkynyl bonds as allowed by chemical bonding rules; and iv. any of geminal $R_q$ can be combined in a double bond to an oxygen;

i. the number of substituents included as $R_q$ will vary depending on n and q in accordance with chemical bonding rules;

j. $R_6$ and $R_7$ may be the same or different and each of $R_6$ and $R_7$ is selected from the group consisting of H, $C_1$–$C_4$ alkyl, $C_3$–$C_4$ alkenyl, $C_3$–$C_4$ alkynyl, $C_3$–$C_6$ cycloalkyl, aryl and $C_1$–$C_4$ alkoxyalkyl, except that $R_7$ can not be H;

k. aryl, as used herein, may be unsubstituted or may have up to three substituents selected from the group consisting of halogen, $C_1$–$C_4$ alkyl, $C_2$–$C_4$ alkenyl, $C_3$–$C_6$ cycloalkyl, cyano, $C_1$–$C_4$ haloalkyl, hydroxy, $C_1$–$C_3$ alkoxy, $C_1$–$C_3$ haloalkoxy and aryloxy; and l. when stereocenters are formed by various substitution patterns as described herein, all isomers are included in the definitions for the structure of Formula I.

32. The method of claim 31 in which Z is H.

33. The method of claim 31 in which each X is H or 5-fluoro.

34. The method of claim 31 in which each of $R_1$–$R_5$ is H.

35. The method of claim 31 in which at least one of $R_1$ and $R_2$ is other than hydrogen.

36. The method of claim 31 in which at least two of $R_{3-5}$ is other than hydrogen.

37. The method of claim 36 in which at least one of $R_1$ and $R_2$ is other than hydrogen.

38. The method of claim 31 in which the acylated aminosalicylamides do not include L-Glutamic acid, N-[3-(formylamino)-2-hydroxybenzoyl]-, dipropyl ester; L-Glutamic acid, N-[3-(formylamino)-2-hydroxybenzoyl]-, dibutyl ester; L-Aspartic acid, N-[3-(formylamino)-2-hydroxybenzoyl]-, bis(2,2-dimethylpropyl) ester; Benzamide, 3-(formylamino)-2-hydroxy-N-pentyl-; Benzamide, 3-(formylamino)-2-hydroxy-N-butyl-; Benzamide, 3-(formylamino)-2-hydroxy-N-octyl-; Benzamide, 3-(formylamino)-2-hydroxy-N-decyl-; Benzamide, 3-(formylamino)-2-hydroxy-N-dodecyl-; Benzamide, 3-(formylamino)-2-hydroxy-N-hexyl-.

39. A method for the control or prevention of fungal infestation, which method comprises applying to the locus of the fungus, or the locus in which the infestation is to be controlled or prevented, a fungicidally effective amount of the composition of claim 29.

* * * * *